United States Patent
Guo et al.

(10) Patent No.: US 11,369,307 B2
(45) Date of Patent: Jun. 28, 2022

(54) VESTIBULAR SYSTEM EXAMINATION DEVICE

(71) Applicant: Kaohsiung Medical University, Kaohsiung (TW)

(72) Inventors: Lan-Yuen Guo, Kaohsiung (TW); Chen-Wen Yen, Kaohsiung (TW); Lih-Jiun Liaw, Kaohsiung (TW); Chin-I Huang, Kaohsiung (TW); Cheng-Chun Chen, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 201 days.

(21) Appl. No.: 16/004,904

(22) Filed: Jun. 11, 2018

(65) Prior Publication Data

US 2019/0231245 A1    Aug. 1, 2019

(30) Foreign Application Priority Data

Jan. 29, 2018 (TW) ................ 107103064

(51) Int. Cl.
| | |
|---|---|
| *A61B 5/00* | (2006.01) |
| *A61B 3/113* | (2006.01) |
| *A61B 5/398* | (2021.01) |
| *G06F 3/01* | (2006.01) |

(52) U.S. Cl.
CPC .......... *A61B 5/4023* (2013.01); *A61B 3/113* (2013.01); *A61B 5/398* (2021.01); *A61B 5/4863* (2013.01); *G06F 3/013* (2013.01)

(58) Field of Classification Search
CPC ..... A61B 5/4023; A61B 3/113; A61B 5/4863; A61B 5/0496; G06F 3/013
See application file for complete search history.

(56) References Cited

U.S. PATENT DOCUMENTS

| | | | | |
|---|---|---|---|---|
| 3,716,046 A | * | 2/1973 | Janeke | A61B 5/4863 |
| | | | | 600/546 |
| 2004/0097839 A1 | * | 5/2004 | Epley | A61B 5/1126 |
| | | | | 600/595 |
| 2015/0064670 A1 | * | 3/2015 | Merfeld | A61B 5/70 |
| | | | | 434/236 |
| 2016/0167672 A1 | * | 6/2016 | Krueger | A61B 5/7282 |
| | | | | 340/576 |
| 2017/0136842 A1 | * | 5/2017 | Anderson | B60G 17/0195 |

OTHER PUBLICATIONS

Moog Industrial Group, "Electrifying the Feel of Flight," 2009, Penton Media Inc., p. 2 (Year: 2009).*

* cited by examiner

*Primary Examiner* — Devin B Henson
*Assistant Examiner* — Justin Xu

(57) ABSTRACT

A vestibular system examination device includes a platform unit and an examination unit. The platform unit includes a base, a driving mechanism mounted to the base, and a seat mounted to the driving mechanism and adapted for a user to sit thereon. The seat is driven movably and rotatably with six degrees of freedom by the driving mechanism. The examining unit includes a detector adapted for detecting eye movement or electrooculography of the user, a measuring module electrically connected to the platform unit for measuring location and displacement thereof, and a processing module electrically connected to the detector and the measuring module for receiving and processing data acquired from the detector and the measuring module.

10 Claims, 4 Drawing Sheets

VESTIBULAR SYSTEM EXAMINATION DEVICE

CROSS-REFERENCE TO RELATED APPLICATION

This application claims priority of Taiwanese Patent Application No. 107103064, filed on Jan. 29, 2018.

FIELD

The disclosure relates to an examination device, and more particularly to a vestibular system examination device.

BACKGROUND

The vestibular system is a sensory system responsible for dictating the sense of balance and spatial orientation of an individual. The vestibular system contains the semicircular canals that detect angular acceleration/deceleration of the head and the otolithic organs that sense linear acceleration. When the vestibular system is damaged, a patient may experience postural instability or loss of balance, often accompanied by nausea and vertigo.

Usually, defects in the vestibular system are accompanied by pathologic nystagmus, a condition of involuntary eye movement. Referring to FIG. 1, a rotatory chair testing, a conventional vestibular system examination method, is used to examine the severity of the defects by examining the eye movement of the patient during the test. After the patient (A) is seated in a revolving chair 1 with his/her head tilted thirty degrees forward, the patient (A) is rotated ten turns in twenty seconds, soon followed by an abrupt stop for observing the nystagmus. In this case, the optokinetic nystagmus is expected to be observed.

However, as the rotatory chair testing is fixed to be capable of only horizontal rotation, it is only capable of detecting nystagmus resulted from the lateral semicircular canals other than the anterior and posterior ones. In addition, the rotatory chair testing is often manually operated, in which every testing may have a variety of confounding factors that undermines the objectiveness and the accuracy of the test itself.

SUMMARY

Therefore, an object of the disclosure is to provide a vestibular system examination device that can alleviate the drawback of the prior art.

According to the disclosure, the vestibular system examination device includes a platform unit and an examining unit. The platform unit includes a base, a driving mechanism that is mounted to the base, and a seat that is mounted to the driving mechanism and that is adapted for a user to sit thereon. The seat is driven movably and rotatably with six degrees of freedom by the driving mechanism. The examining unit includes a detector that is adapted for detecting eye movement or electrooculography of the user, a measuring module that is electrically connected to the platform unit for measuring location and displacement thereof, and a processing module that is electrically connected to the detector and the measuring module for receiving and processing data acquired from the detector and the measuring module.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
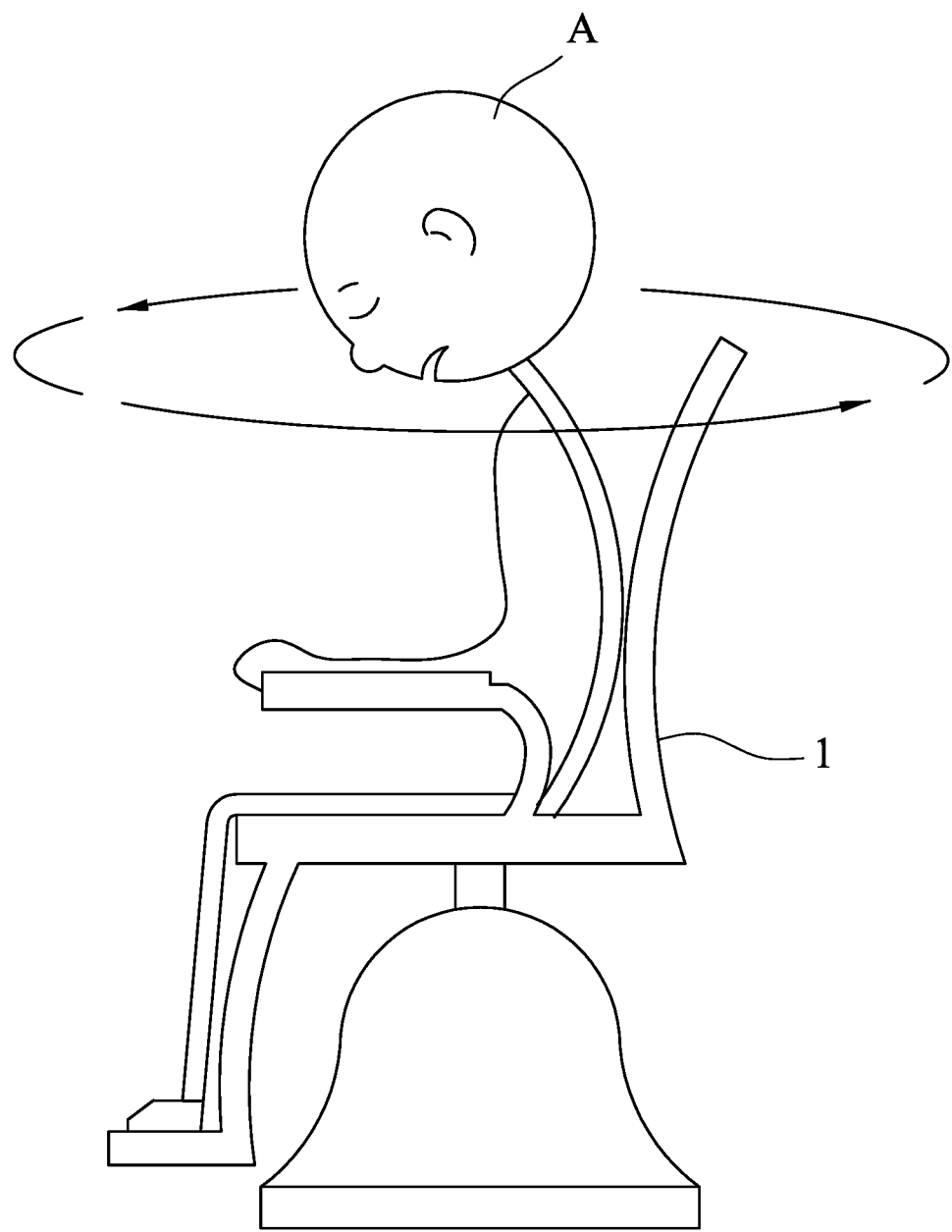
FIG. 1 is a schematic view of a conventional vestibular system examination method.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
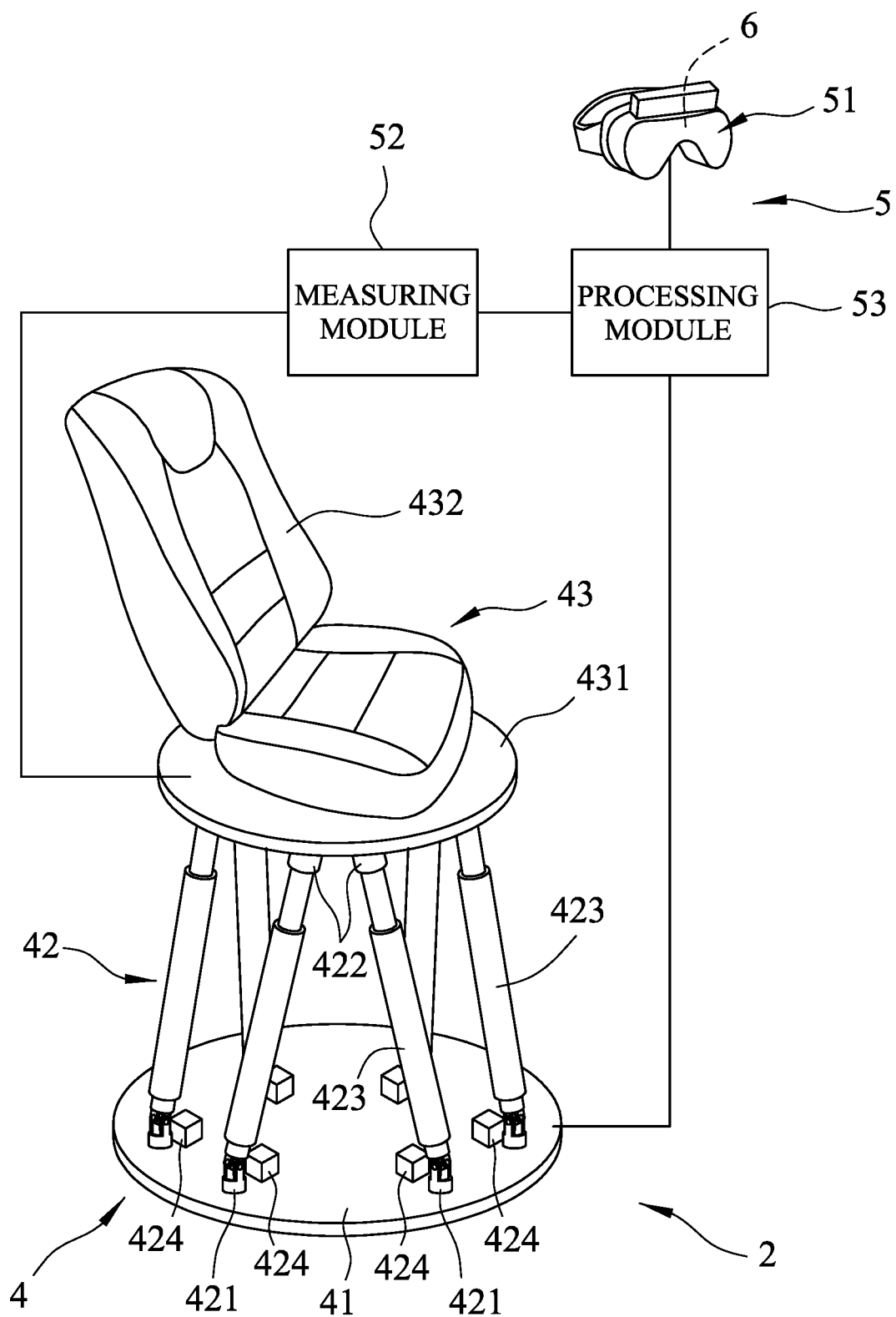
FIG. 2 is a perspective view of a first embodiment of a vestibular system examination device according to the disclosure.
Figure 3:
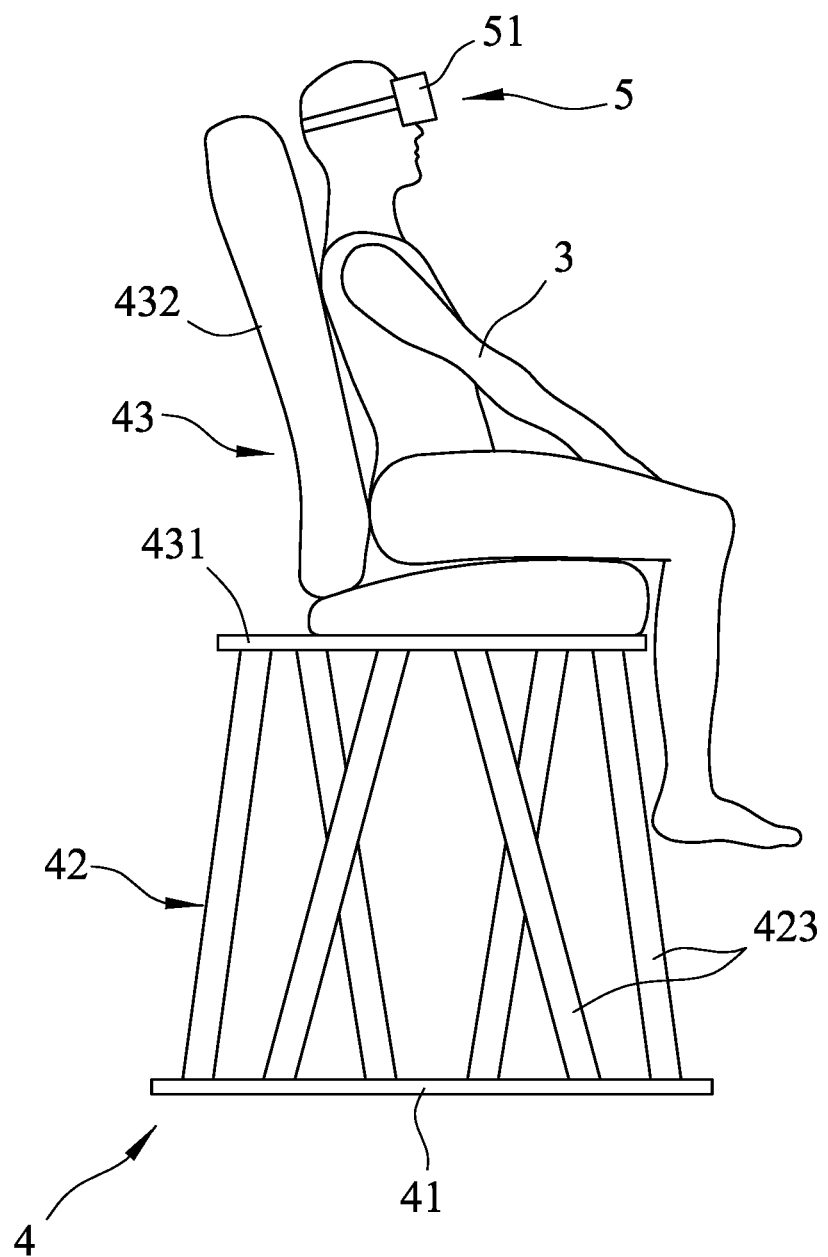
FIG. 3 is a schematic view of the first embodiment in use.

Referring to FIGS. 2 and 3, a first embodiment of a vestibular system examination device 2 according to the disclosure includes a platform unit 4 and an examining unit 5.

The platform unit 4 includes a base 41, a driving mechanism 42, and a seat 43. The driving mechanism 42 includes six lower connectors 421, six upper connectors 422, six linkage members 423, and six servo motors 424. The lower connectors 421 are mounted on a top surface of the base 41, and the upper connectors 422 are mounted on a bottom surface of the seat 43. Both the lower and upper connectors 421, 422 are universal joints. It should be noted that, while upper portions of the upper connectors 422 are blocked from view in FIG. 2, the upper connectors 422 are structurally identical to the lower connectors 421. For the sake of brevity, details of the lower and upper connectors 421, 422 are not drawn in FIG. 3. Each of the linkage members 423 is a hydraulic cylinder that extends along a longitudinal axis, and has opposite ends that are mounted pivotally and respectively to a respective one of the lower connectors 421 and a respective one of the upper connectors 422. Each of the servo motors 424 is mounted on the top surface of the base 41 and actuates a respective one of the linkage members 423 to be extendible along the longitudinal axis, such that the linkage members 423 are operable to drive movement and rotation of the seat 43 with six degrees of freedom. The seat 43 has a pedestal portion 431 that is connected to the upper connectors 422 of the driving mechanism 42, and a seat portion 432 that is mounted on a top surface of the pedestal portion 431 and that is adapted for a user 3 to sit thereon.

The examining unit 5 includes a detector 51 that is adapted to be worn on the user's head for detecting eye movement of the user 3, a measuring module 52 that is electrically connected to the seat 43 of platform unit 4 for measuring location and displacement thereof, and a processing module 53 that is electrically connected to the linkage members 423 and the servo motors 424 of the driving mechanism 42, the detector 51 and the measuring module 52. It should be noted that, the electric connection between the processing module 53 and the linkage members 423 is not visually exemplified in FIG. 2 to avoid cluttering of lines thereon. In the first embodiment, the detector 51 is one of an electrooculography instrument and a video-based eye tracker for detecting and measuring presence of nystagmus in the user 3.

During examination of the vestibular system, the servo motors 424 is initiated to actuate each of the linkages members 423 to displace and tilt based off preset parameters while the user 3 remained seated on the seat portion 432 of the seat 43. If the detector 51 detects the presence of the nystagmus during the process, an electrooculography measured by the detector 51 and measured location and displacement data from the measuring module 52 are to be received and processed by the processing module 53. By comparing the two types of data, the processing module 53 records location, movement and velocity in which the nystagmus is triggered for the user 3.

A prototype of the first embodiment has been utilized in an experiment to compare nystagmus and voluntary left-and-right eye movement of the user 3. Unlike voluntary eye movement, nystagmus is observed by the prototype to move in a smaller scale, distinctly displaying smaller energy in frequency domain of the electrooculography compared to that of the voluntary movement. Once the presence of the nystagmus is identified, the user 3 is then driven movably and rotatably, with six degrees of freedom, in a specific direction that corresponds to the orientation of each of semicircular canals in the vestibular system to ensure the thoroughness and accuracy of the examination.

In addition to examining presence of the nystagmus, the processing module 53 has information (location, movement and velocity) in which the user 3 experiences the vertigo associated with the nystagmus, the vestibular system examination device 2 may also mimic traditional vestibular rehabilitation techniques (such as Cawthorne-Cooksey maneuver) in treating the user 3 to overcome the vertigo. To do so, the processing module 53 actuates the driving mechanism 42 to expose the user 3 to the same motion repetitively and progressively faster each time. Ideally, the vestibular system of the user 3 may become more adapted and habituated to the motion, such that experiencing the same motion will no longer induce the vertigo.

The vestibular system examination device 2 further includes a display 6 mounted on the detector 51 for displaying images of virtual environment. Preferably, the detector 51 is manufactured as headgear such as a blindfold or a helmet, with the display 6 covering the user's vision. As the display 6 is electrically connected to the processing module 53 through the detector 51, the display 6 may realign view within the images based off displacement of the seat 43. For example, if the seat 43 rotates to the left, the display 6 will realign the view to the left as well to simulate a realistic environment. The virtual environment is helpful in assisting the user 3 to be immersed elsewhere, enhancing the efficiency of the rehabilitation program.

Overall, the first embodiment of the vestibular system examination device 2 is capable of producing the electrooculography that is accurately representative of the nystagmus experienced by the user 3, The electrooculography may be further referenced throughout a treatment program designated to the user 3 for evaluating the progress of the rehabilitation.

Figure 4:
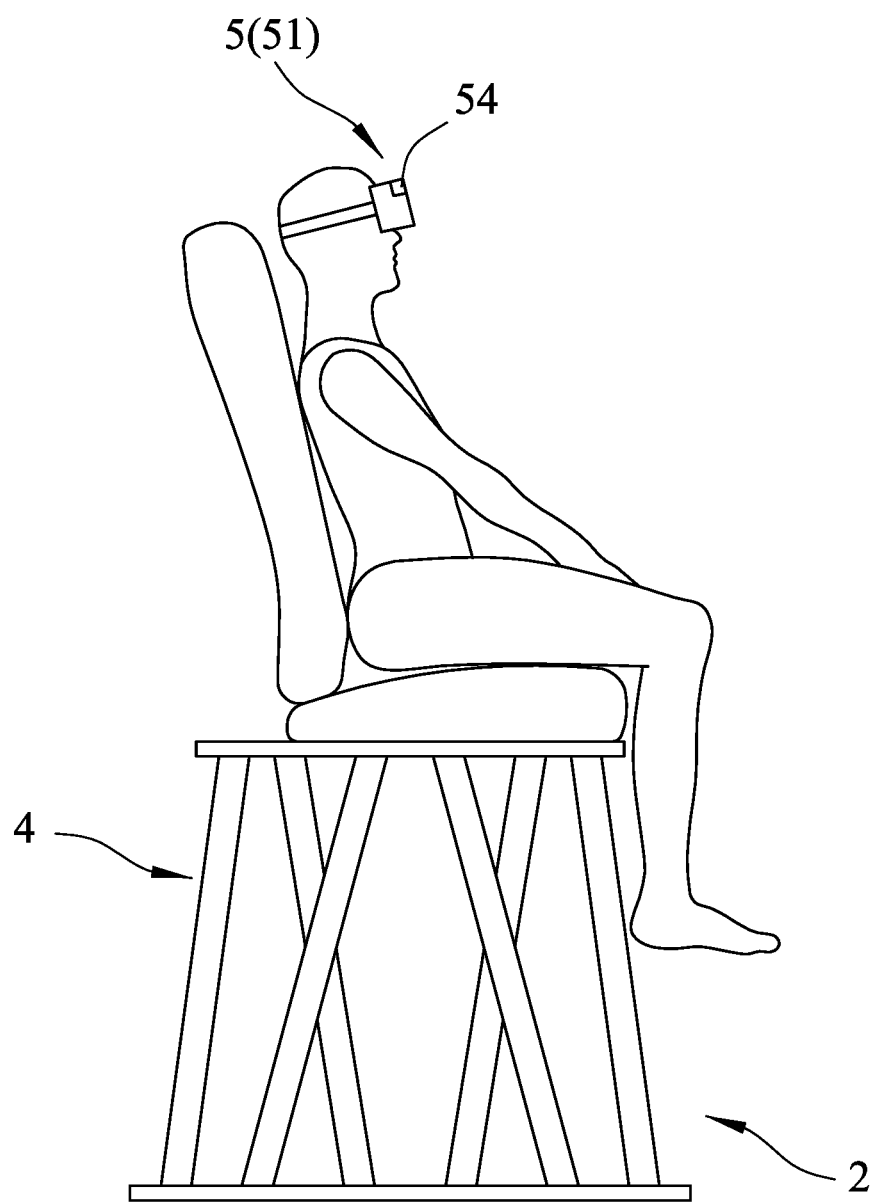
FIG. 4 is a schematic view of a second embodiment of the vestibular system examination device in use.

Referring to FIG. 4, a second embodiment of the disclosure is similar to that of the first embodiment. In this embodiment, the examining unit 5 further includes a recording module 54 that records images of the user's eye movement when the platform unit 4 is in operation. In this embodiment, the recording module 54 is a high-speed camera with eye-tracking capability, and is worn by the user 3 as a headgear. In other embodiments, the recording module 54 is not restricted as such. The images recorded may be referenced when building the treatment program.

For both embodiments, the following parameters may be implemented in the platform unit 4 of the vestibular system examination device 2 when the user 3 is driven movably and rotatably by the driving mechanism 42:

1. With the user's head being affixed and the user's eyes staring at a fixed point, an oscillating pulse formed by the motion actuated by the platform unit 4, is to be delivered to the user 3 with the user's head as instant center of rotation. The oscillating pulse is set with an acceleration of 3000 to 4000 degrees per second squared, at an oscillating angle of 10 to 20 degrees in all three principal axes (yaw, pitch and roll).

2. In the first 100 milliseconds, the head of the user 3 should oscillate relative to the body at an oscillating angle of 15 to 20 degrees, with the peak velocity of 200 to 300 degrees per second and a peak acceleration of 2500 to 4500 degrees per second squared.

The abovementioned parameters in the platform unit 4, in conjunction with the recording module 54, may trigger the nystagmus of the user 3 for further examination of the vestibular system. In other embodiment, a different set of parameters may be used.

In summary, by utilizing the driving mechanism 42 to drive the seat 43 movably and rotatably with six degrees of freedom, all of the semicircular canals of the vestibular system may be thoroughly examined for presence of the nystagmus. With the processing module 53 recording conditions in which the nystagmus is triggered, in addition to performing a more thorough examination of the vestibular system to determine the severity of the nystagmus, the vestibular system examination device 2 may further treat the user 3 from the vertigo associated with the nystagmus.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A vestibular system examination device comprising:
   a platform unit including a base, a driving mechanism that is mounted to said base, and a seat that is mounted to said driving mechanism and that is adapted for a user to sit thereon, said seat being driven movably and rotatably with six degrees of freedom by said driving mechanism; and
   an examining unit including a detector that is adapted for detecting eye movement or electrooculography of the user so as to detect and measure the presence of nystagmus in the user, a measuring module that is electrically connected to said platform unit for measuring location and displacement thereof, and a processing module that is electrically connected to said detector and said measuring module for receiving and processing data acquired from said detector and said measuring module, wherein said processing module is configured to operate in an examination phase and a rehabilitation phase, and in the examination phase, the data acquired from said detector and said measuring module are compared, and conditions under which the nystagmus is triggered are recorded, where the conditions are related to the location and displacement of said platform unit measured by said measuring module, by comparing the two types of data acquired from said detector and said measuring module, the processing module recording location, movement and velocity in which the nystagmus is triggered for the user, and in the rehabilitation phase, the processing module is configured to actuate the driving mechanism according to the conditions recorded.

2. The vestibular system examination device as claimed in claim 1, wherein said driving mechanism of said platform unit includes:

six lower connectors that are mounted on a top surface of said base;

six upper connectors that are mounted on a bottom surface of said seat; and six linkage members, each of said linkage members extending along a longitudinal axis, being extendible along the longitudinal axis, and having opposite ends that are mounted pivotally and respectively to a respective one of said lower connectors and a respective one of said upper connectors, such that said linkage members being operable to drive movement and rotation of said seat with six degrees of freedom.

3. The vestibular system examination device as claimed in claim 2, wherein said lower and upper connectors of said driving mechanism of said platform unit are universal joints.

4. The vestibular system examination device as claimed in claim 2, wherein said seat of said platform unit has a pedestal portion that is connected to said driving mechanism, and a seat portion that is mounted on a top surface of said pedestal portion and that is adapted for the user to sit thereon.

5. The vestibular system examination device as claimed in claim 1, wherein said detector of said examining unit is one of an electrooculography instrument and a video-based eye tracker.

6. The vestibular system examination device as claimed in claim 1, wherein said examining unit further includes a recording module that records images of the user's eye movement when said platform unit is in operation.

7. The vestibular system examination device as claimed in claim 1, further comprising a display for displaying images of virtual environment, said display realigning view within the images based off displacement of said seat.

8. The vestibular system examination device as claimed in claim 7, wherein said detector of said examining unit is adapted to be worn on the user's head, and said display is mounted on said detector within the user's view.

9. The vestibular system examination device as claimed in claim 1, wherein in the rehabilitation phase, the processing module is configured to actuate the driving mechanism to expose the user to motions repetitively according to the conditions recorded.

10. The vestibular system examination device as claimed in claim 9, wherein the motions are progressively faster while being repeated.

* * * * *